United States Patent [19]

Reusser et al.

[11] 4,343,906
[45] Aug. 10, 1982

[54] HYBRID PLASMID OF PBR322 AND STREPTOMYCES PLASMID AND E. COLI CONTAINING SAME

[75] Inventors: Fritz Reusser, Portage; Vedpal S. Malik, Kalamazoo, both of Mich.

[73] Assignee: The Upjohn Company, Kalamazoo, Mich.

[21] Appl. No.: 68,418

[22] Filed: Aug. 21, 1979

[51] Int. Cl.³ .............................................. C12N 1/20
[52] U.S. Cl. .................................... 435/253; 435/172; 435/317
[58] Field of Search ........................ 435/172, 253, 317

[56] References Cited

U.S. PATENT DOCUMENTS 4,237,224 12/1980 Cohen et al. ...................... 435/183

OTHER PUBLICATIONS

Malik, The Journal of Antibiotics, vol. XXX, No. 10, pp. 897–899, (1977).
Clarke et al., Proc. Natl. Acad. Sci., U.S.A., vol. 72, No. 11, pp. 4361–4365, Nov. 1975.
Maniatis et al., Cell., vol. 15, p. 687, Oct. 1978.

*Primary Examiner*—Alvin E. Tanenholtz
*Attorney, Agent, or Firm*—Roman Saliwanchik

[57] ABSTRACT

A process for cloning DNA into a suitable host, which comprises fragmenting said DNA to obtain fragmented DNA, ligating said fragmented DNA into a suitable vector to obtain chimeric (hybrid) DNA, and transforming said chimeric DNA into said ultimate host. By this process, the useful chemical plasmid pUC3, which is obtainable from a biologically pure culture of the microorganism Streptomyces sp. 3022a, NRRL 11441, is cloned into the well-known bacterium *E. coli* HB101. This cloning of pUC3 into *E. coli* HB101 enables the production of large amounts of plasmid pUC3 DNA. pUC3 is useful as a cloning vehicle in recombinant DNA work. For example, using recombinant DNA methodology, a desired gene, for example, the insulin gene, can be inserted into pUC3 and the resulting plasmid can then be transformed into a suitable host microbe which, upon culturing, produces the desired insulin.

6 Claims, 1 Drawing Figure

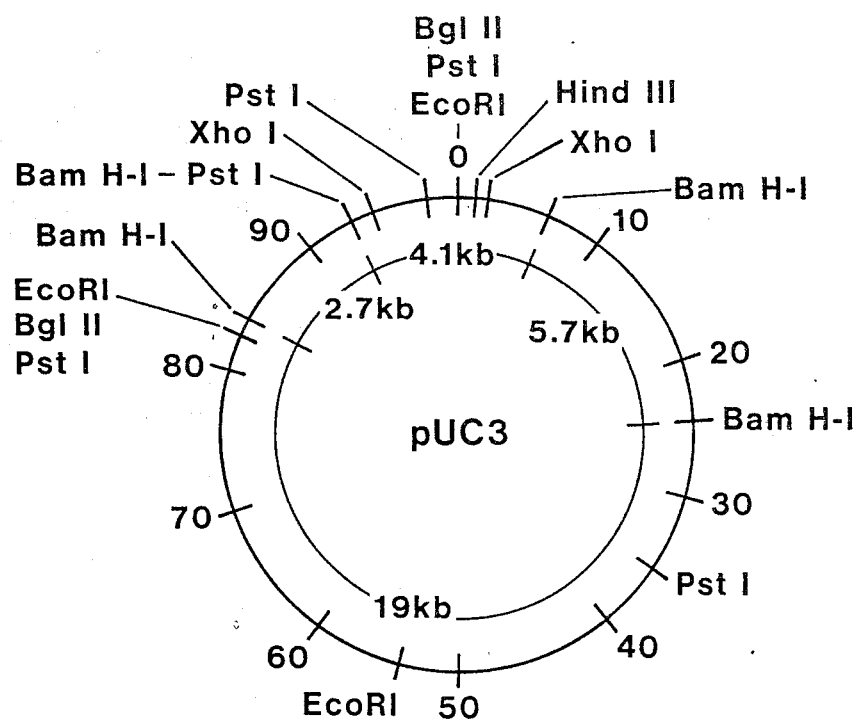

HYBRID PLASMID OF PBR322 AND STREPTOMYCES PLASMID AND E. COLI CONTAINING SAME

BACKGROUND OF THE INVENTION

It is well known that DNA in some microbes, for example some streptomycetes, contains genes responsible for antibiotic synthesis. Attempts to clone such DNA into a suitable host, for example, E. coli HB101, has not heretofore been accomplished. It is believed that the presence of lethal gene(s), i.e., gene(s) responsible for antibiotic synthesis, interfere with the cloning process. It is recognized that there may be other factors which prevent the successful cloning.

The process of the subject invention solves the above problem by fragmenting the DNA prior to cloning the DNA into a suitable host. The DNA described herein is essentially pure plasmid pUC3 which is obtainable from a biologically pure culture of the microorganism Streptomyces sp. 3022a, NRRL 11441. Plasmid pUC3 has a molecular weight of approximately $20 \times 10^6$ daltons.

BRIEF SUMMARY OF THE INVENTION

Plasmid pUC3, which is obtainable from the microorganism Streptomyces sp. 3022a, NRRL 11441, is cloned into E. coli HB101. S. sp. 3022a, NRRL 11441 produces the antibiotic chloramphenicol which is active against E. coli HB101. The cloned streptomycetes plasmid, i.e. pUC3, could contain the genes involved in biosynthesis of chloramphenicol which is lethal to E. coli HB101. This is the first known case where such DNA has been cloned and replicated into a susceptible host. The constructed plasmid chimeras of the subject invention can be easily isolated in large quantities from E. coli, e.g. 30-300 copies per cell as opposed to only 5-10 copies per cell in the streptomycete.

The entire plasmid genome is cloned into E. coli HB101 by the construction of several clones containing specific fragments of the pUC3 plasmid using plasmid pBR322 as a vector. The full length circular plasmid pUC3 contains approximately 30 kb pairs per total length of the genome. Digestion with Bam H-I yields four fragments 19, 5.7, 4.1 and 2.7 kb pairs in length. pUC1009 contains the 19 kb fragment of pUC3 and pBR322; pUC1010 contains the 5.7 kb fragment of pUC3 and pBR322; and pUC1011 contains the 5.7, 4.1 and 2.7 kb fragments and pBR322. None of the constructed E. coli clones produces chloramphenicol in detectable amounts. Also, a test for antibiotic resistance markers has shown that none of the clones carries resistance markers against commonly used antibiotics, i.e. neomycin, nalidixic acid, spiramycin, tetracycline, chloramphenicol, novobiocin, oleandomycin, spectinomycin, carbomycin, gentamycin, cephaloridine, bacitracin, and streptomycin.

The fragments of pUC3 are cloned into E. coli HB101 using the well-known plasmid pBR322 (having a single Bam H-I site) as a vector.

The availability of these new clones enables the production of large amounts of plasmid pUC3 DNA because pBR322 is present in many copies in E. coli HB101.

pUC3 is useful as a cloning vector in DNA work wherein desired genes are incorporated into the plasmid, and the plasmid then transformed into a suitable host.

In its broadest aspect, the process of the subject invention is a process for cloning DNA into a suitable host, which comprises fragmenting said DNA to obtain fragmented DNA, ligating said fragmented DNA into a suitable vector to obtain chimeric DNA, and transforming said chimeric DNA into said ultimate host.

REFERENCE TO THE DRAWING

The drawing depicts the restriction endonuclease cleavage map for pUC3 and the fragments of the plasmid described herein as cloned into E. coli HB101. The map is constructed on the basis of plasmid pUC3 having a molecular weight of $20 \times 10^6$ daltons or a molecular length of 30 kilobase pairs. The map positions of the various restriction sites are given as percentages, the total plasmid length being 100 percent. One of the Eco RI sites is assigned position 0 percent on the circular map.

The restriction endonuclease abbreviations are as follows:

(1) Eco RI is an enzyme from *Escherichia coli;*
(2) Hind III is an enzyme from *Hemophilus influenzae*
(3) Xho I is an enzyme from *Xanthomonas holcicola;*
(4) Pst I is an enzyme from *Providencia stuartii;*
(5) Bgl II is an enzyme from *Bacillus globigii;* and
(6) Bam-HI is an enzyme isolated from *Bacillus amyloliquefaciens.*

DETAILED DESCRIPTION OF THE INVENTION

The Microorganisms and Plasmids

The following microorganisms are available from the permanent collection of the Northern Regional Research Laboratory, U.S. Department of Agriculture, Peoria, Ill., U.S.A.

| | |
|---|---|
| NRRL B-11371 | E. coli HB101 |
| NRRL B-11441 | S. sp. 3022a |
| NRRL B-12005 | E. coli HB101 (pUC1009) |
| NRRL B-12006 | E. coli HB101 (pUC1010) |
| NRRL B-12007 | E. coli HB101 (pUC1011) |
| NRRL B-12014 | E. coli RR1 (pBR322) |

These deposits are available to the public upon the grant of a patent to the assignee, The Upjohn Company, disclosing them. The deposits are also available as required by foreign patent laws in countries wherein counterparts of the subject application, or its progeny, are filed. However, it should be understood that the availability of a deposit does not constitute a license to practice the subject invention in derogation of patent rights granted by governmental action.

Characteristics of Plasmid pUC3

Molecular Weight: ca. $20 \times 10^6$ daltons.

Restriction Endonuclease Sensitivities pUC3 has the following sensitivities to restriction endonucleases. (Please refer to the drawing for the restriction endonuclease cleavage map for pUC3.)

Plasmid Sensitivities To Restriction Endonucleases

| | # Cleavage Sites | | # Cleavage Sites |
|---|---|---|---|
| Enzyme | pUC3 | Enzyme | pUC3 |
| Bgl I | Many* | Bgl II | 4 |
| Bam HI | 4 | Hpa I | 0 |

-continued

| # Cleavage Sites | | # Cleavage Sites | |
|---|---|---|---|
| Enzyme | pUC3 | Enzyme | pUC3 |
|  |  | Hind III | 1 |
| Eco RI | 3 | Knp I | >5 |
| Pst I | 5 | Pvu II | 9 |
| Mbo II | Many | Ava I | Many |
| Xba I | None | Xho I | 2 |
| Sal I | Many | Hph I | Many |
| Hae II | >7 | Hinf I | Many |
| Sma I | Many | Hinc II | Many |

*Used to denote more than 10 sites.

These results were obtained by digestion of DNA in the presence of an excess of restriction endoculease. The number of restriction sites were determined from the number of resolvable fragments in either 0.7 or 1.0% agarose gels.

The full length circular plasmid pUC3 contains approximately 30 kb pairs per total length of the circular genome. Digestion with Bam H-I yields four fragments, i.e., 19, 5.7, 4.1 and 2.7 kb pairs in length. These fragments were cloned into E. coli HB101 (NRRL B-11371) using the plasmid pBR322 as a vector. Clones containing the 19 or 5.7 kb fragments are isolated and designated as E. coli NRRL B-12005 and NRRL B-12006, respectively. The cloning of the two smallest fragments of pUC3, i.e., 4.1 and 2.7 kb, was not successful for unknown reasons. In order to overcome this and still clone the entire pUC3 genome into E. coli, a limited Bam H-I digest of plasmid pUC3 DNA was prepared. This led to the formation of incomplete or partial digestion products. Specifically, a Bam H-I fragment was obtained with a total length of about 12.5 kb and consisting of the 5.7, 4.1 and 2.7 kb Bam fragments. This digestion mixture was ligated with pBR322 vector DNA and transformed into E. coli HB101. The resulting clone is designated as E. coli NRRL B-12007.

A restriction enzyme map for plasmid pUC3 which depicts the fragments is provided herein.

Vector pBR322 DNA can be isolated from E. coli NRRL B-12014 by the following procedure.

A 100 ml culture of E. coli HB101 (pBR322) is grown overnight in L-broth which consists of the following ingredients:

| Bacto tryptone (Difco) | 10 g/liter |
|---|---|
| Bacto yeast extract (Difco) | 5 g/liter |
| NaCl | 5 g/liter |
| Ampicillin | 50 mg/liter |

The cells are recovered by centrifugation at 17,000×g for 10 minutes in a refrigerated centrifuge. The pellet is suspended in 2.5 ml 50 mM tris buffer (pH8) containing 25% sucrose. One-half ml of lysozyme stock solution is added (5 mg/ml in TES buffer). The mixture is allowed to stand in ice for 5 minutes. At this point 1 ml EDTA (0.25 M, pH8) is added and the mixture is again allowed to stand in ice for 5 minutes. One and a quarter ml of 5 N NaCl and 1 ml 10% SDS (sodium dodecyl sulfate) are then added. The mixture is shaken on a Vortex and incubated at 37 C. for 20 minutes. Then 10 μl of ribonuclease (20 mg/ml) is added and the sample is again incubated at 37 C. for 20 minutes. The mixture is then kept in ice overnight and then centrifuged at 35,000×g for 30 minutes in a refrigerated centrifuge. 2 ml of the supernatant solution (lysate) are carefully removed with a pipette. Four and one-half ml of TES buffer (30 mM tris.HCl, pH8, 5 mM EDTA.-Na$_2$, 50 mM NaCl) are mixed with 1.5 ml EtBr (ethidium bromide) stock (1 mg/ml in TES buffer) and 7.5 g solid CsCl. After the salt had dissolved, 2 ml of the lysate, described above, is added and the mixture is transferred into a polyallomer tube fitting a titanium 50 (Ti 50) head (Beckman ultracentrifuge). The tubes are filled to the top with mineral oil and centrifuged in a Beckman ultracentrifuge at 40,000 rpm in a Ti 50 head at 20 C. for at least 2 days. The DNA is located under a long wave UV-lamp and the heavier band containing the plasmid DNA is removed with a syringe by puncturing the tube wall from the side. The samples are extensively dialysed against 100 volumes of TES buffer at 4 C. Following dialysis 1/10 sample volume of a 3 N NaCl stock solution is added and the plasmid DNA is precipitated by the addition of 2 volumes of cold ethanol. The resulting pellet is then lyophilized and redissolved in 200 μl 10 mM tris buffer, pH7.8 containing 1 mM EDTA.Na$_2$ and frozen for storage.

The following examples are illustrative of the process and products of the subject invention but are not to be construed as limiting. All percentages are by weight and all solvent mixture proportions are by volume unless otherwise noted.

EXAMPLE 1—Cloning Of Streptomycete Plasmid pUC3 Into E. coli HB101

Plasmid pBR322 DNA is digested with Bam restriction enzyme by mixing 4 μl of DNA (0.3 μg/μl), 12 μl (double distilled H$_2$O (DD.H$_2$O), 2 μl 10× high salt restriction buffer (Post et al., Cell 15, 215–229, 1978) and two μl of Bam solution. This mixture is incubated at 37 C. for 1 hour. Five μl of bacterial alkaline phosphatase (BAP.F, Worthington) is then added and the mixture is incubated at 65 C. for 10 minutes. Following the nuclease treatment, 350 μl of 10 mM Tris.acetate, pH7.8, and 40 μl of 3 M Na. acetate stock solution are added. The sample is extracted three times with an equal volume of phenol, precipitated with ethanol, lyophilized and redissolved in 10 mM tris buffer. This solution is used for the ligation reaction described below.

Plasmid pUC3 DNA is subjected to Bam digestion in a reaction mixture containing 5.4 μl pUC3 DNA (0.6 μg/μl), 10.6 μl DD.H$_2$, 2 μl 10× high salt restriction buffer and 2 μl Bam solution. This mixture is kept at 37 C. for 1 hour. The reaction is stopped by incubating the sample at 65 C. for 10 minutes. The solution, which contains pUC3 fragments, described above, is then used for the ligation reaction.

For ligation, 10 μl pBR322 digestion mix, 20 μl pUC3 digestion mix and 20 μl DD.H$_2$O are combined. Ten μl 0.5 M Tris.HCl, pH7.8, 20 μl 100 mM DDT, 10 μl 100 mM MgCl$_2$ and 10 μl 10 mM ATP are mixed separately and then combined with the restricted DNA mixture. Finally, 1.5μ of T$_4$ DNA ligase is added and the sample is kept in ice for 1–2 days. Following ligation, the solution is adjusted to 0.3 M with Na.acetate and the DNA precipitated with ethanol. The pellet is washed in ethanol and lyophilized. The DNA is redissolved in 200 μl transformation buffer containing 10 mM Tris.HCl, pH7, 10 mM CaCl$_2$ and 10 mM MgCl$_2$.

For transformation into E. coli HB101, seed is grown overnight in L-broth and diluted 1:100 into fresh L-broth the next day. The cells are incubated at 37 C. and allowed to grow to an OD$_{600}$ of 0.6. At this point 50 ml of culture is centrifuged in the cold, the pellet resuspended in 25 ml cold 10 mM MgSO4 and centrifuged again. The pellet is then resuspended in 25 ml cold 50 mM CaCl2 solution and kept on ice for 20 minutes. After centrifugation the cells are resuspended in 5 ml cold 50 mM CaCl2 solution. One hundred μl of ligase mixture (see above) is mixed with 200 μl cell suspension. This mixture is kept in ice for 15 minutes, heated to 42 C. for 2 minutes and then left at room temperature for 10 minutes. Ten μl aliquots are plated on freshly prepared agar plates containing 25 ml of L-broth, 1.5% agar, and 50 μg of ampicillin/ml. Colonies are selected and scored for tetracycline sensitivity.

Colonies are screened for the presence of plasmids of different sizes by making a small amount of cleared lysate. Single colonies are grown in small cultures overnight. 1 ml culture is centrifuged for 2 minutes in an Eppendorf microcentrifuge. The pellet is resuspended in 25 μl 25% sucrose in 50 mM Tris.HCl, pH8.0. Five μl of a lysozyme solution (5 mg/ml in 10 mM Tris.HCl, pH8.0) is added. After 5 minutes at 0° C. 10 μl 0.25 M EDTA, pH 7.0 is added. After an additional 5 minutes incubation at 0° C., 12.5 μl 5 M NaCl and 5 μl 10% SDS are added and the mixture is quickly shaken by a Vortex mixer. After 1-2 hours at 0° C., the mixture is centrifuged 5 minutes in an Eppendorf microcentrifuge and 20 μl supernatant is digested with 1 μl Bam and analyzed using agarose slab gel electrophoresis. Detection of plasmid DNA and estimation of its approximate size are made by examining gels stained with ethidium bromide under a long-wave ultraviolet lamp in a known manner.

Suspected transformants are then grown in 10 ml cultures. Cleared lysates are prepared as described above. The supernatants are treated with pancreatic RNase A (25 mg/ml, 30 minutes at room temperature), and then extracted with phenol. DNA is precipitated from the aqueous phase by ethanol, and then digested with suitable restriction enzymes to analyze DNA fragments cloned in the transformants.

The pUC3 fragments can be isolated from the new hybrid plasmids by well known procedures using Bam to digest the hybrid plasmid.

EXAMPLE 2—Isolation of Plasmid pUC3 From a Biologically Pure Culture of Streptomyces sp. 3022a, NRRL 11441

Streptomyces sp. 3022a, NRRL 11441, spores are inoculated into 100 ml of the following medium:

| Bacto tryptone | 0.05% |
|---|---|
| Brer rabbit molasses | 1.0% |
| Glycerol | 1.0% |
| Difco yeast extract | 0.25% |

Adjust to pH 7.2 with 1 N NaOH Tap Water to 1000 ml

The medium has previously been sterilized in a 500 ml Erlenmeyer flask. After inoculation, the flask is incubated at 28 C. for about 36 to 48 hours on a Gump rotary shaker operating at 250 rpm.

This cell suspension is used to seed 40 flasks of Glycerol-serine-lactate medium at the rate of 1%. Glycerol-serine-lactate medium has the following composition:

| Glycerol | 2% |
|---|---|
| 60% Sodium lactate | 2.8% |
| DL-Serine | 0.3% |

| -continued | |
|---|---|
| Sodium chloride | 0.6% |
| Difco yeast extract | 0.025% |
| KH2PO4 | 0.14% |
| K2HPO4 | 0.2% |
| MgSO4.7H2O | 0.05% |
| MnSO4.H2O | 0.0008% |
| CuSO4.5H2O | 0.0006% |
| ZnSO4 | 0.0012% |

Adjust pH to 7.0 with 1 N NaOH.

After 3 days incubation at 28° C. the cells are separated from the broth by low speed centrifugation, for example, at 10,000×g for 10 minutes at 4° C., and the supernatant is decanted from the mycelial pellet. The cells are washed once in 250 ml of TES buffer (30 mM Tris.HCl, pH8.0; 5 mM EDTA; 50 mM NaCl). The washed cells are transferred to a Waring blender and 200 ml of a solution containing 25% sucrose, 0.1 M Tris.HCl, pH8.0 and 0.5 mg lysozyme/ml is added. Homogenization is carried out for 1 minute. The homogenate is kept at room temperature for 30 minutes, 100 ml of 0.25 M EDTA.Na2 (pH8.0) is added, and the mixture is allowed to stand for an additional 30 minutes. At this point 320 ml of Brij-DOC solution (1% Brij, 0.04% DOC, 0.06 M EDTA and 50 mM Tris.HCl, pH8.0) is added. The mixture is again allowed to stand at room temperature for 30 minutes and then at 55° C. for the same time period. The resulting viscous lysate is centrifuged at 5° C. for 1 hour at 20,000×g. The supernatant is extracted with an equal volume of phenol saturated with TES buffer. The phases are separated by centrifugation at 5° C. and the aqueous layer is recovered and further extracted with 1 volume of chloroform. The aqueous phase is again recovered after centrifugation and the DNA is precipitated by the addition of 2 volumes of cold ethanol. The precipitate is kept at −20° C. overnight. After centrifugation, the pellet is redissolved in 40 ml of TES buffer containing 2.5 mg of predigested pronase(Calbiochem)/ml. This is followed by the addition of 90 ml of a 2 g/ml CsCl and 10 ml of a 1 mg/ml ethidium bromide stock solution, respectively, both dissolved in TES buffer. The mixture is centrifuged for 35 hours in a Ti 50 rotor at 38,000 rpm and 18° C. The resulting plasmid DNA band is located by exitation with a long wavelength UV light source and is removed by puncturing the tube wall with a small syringe. Ethidium bromide is extracted with a small volume of 1-butanol saturated with H2O. CsCl is then removed by exhaustive dialysis against TES buffer containing 0.5 N NaCl. The DNA is recovered by precipitation with cold ethanol as described above for pBR322. The pellet is redissolved in TES buffer and usually further purified by 1-2 additional ethidium bromide-CsCl centrifugation steps prior to analysis with restriction enzymes. This procedure yields essentially pure covalently cloned circular plasmid pUC3 DNA.

Procedures For Characterizing And Isolating pUC3

The size of pUC3 was determined by electron microscopy.

Restriction Endonuclease Digestion And Agarose Gel Electrophoresis

All the restriction enzymes used were purchased from New England Biolabs.

Digestion of plasmid DNA was performed in restriction buffer containing 10 mM Tris.HCl, pH7.4; 5 mM MgCl$_2$; 1 mM DTT for Ava I, Hph I, Mbo II, Pvu II, Hae II, Kpn I, Hinc II, Hpa I and Bgl II. The same buffer containing 50 mM NaCl was used for Bam H-I, Hinf I, Sal I, Xba I, Bgl I, EcoRI, Xho I, Hind III and Pst I. Sma I digestion mixtures contained 15 mM Tris.HCl, pH9.0; 15 mM KCl; 6 mM MgCl$_2$ (Post, L. E., Arfsten, A. E., Reusser, F. and Nomura, M. 1978. DNA sequences of promotor regions for the str and spc ribosomal protein operons in *E. coli*. Cell 15, 215–229).

The digestion mixtures were analyzed in 1% agarose gels prepared as described by Shinnick et al. (Shinnick, T. M., Lund, E., Smithies, O., and Blattner, F. R. 1975. Hybridization of labeled RNA to DNA is agarose gels. Nucl. Acids Res. 2, 1911–1229).

Hind III-digested λ DNA was used as a molecular weight reference (Murray, K. and Murray, N. E. 1975. Phage Lambda Receptor Chromosomes for DNA Fragments made with Restriction Endonuclease III of *Haemophilus influenzae* and Restriction Endonuclease I of *Escherichi coli*. J. Mol. Biol. 98, 551–564).

Examples of other vectors which can be used in the invention are pBR313 which codes for ampicillin and tetracycline resistance, pSC101 which codes for tetracycline resistance, pCR11 which codes for kanamycin resistance. λ bacteriophage vectors, for example, charon phages, and yeast 2μ plasmid DNA.

Examples of other hosts for the vector are any *E. coli* K-12 derivatives [Bacteriological Reviews, Dec. 1972, pages 525–557] (these have been approved by the NIH Guidelines) and yeasts, other fungi, or other bacteria. It is recognized that these latter hosts would also have to be approved by the NIH Guidelines.

pUC3 can be used to create recombinant plasmids which can be introduced into host bacteria by transformation. The process of creating recombinant plasmids is well known in the art. Such a process comprises cleaving the isolated plasmid, e.g., pUC3, at one specific site by means of a restriction endonuclease, for example, Hind III. The plasmid, which is a circular DNA molecule, is thus converted into a linear DNA molecule by the enzyme which cuts the two DNA strands at sites which can be several base pairs apart. Another plasmid is similarly cleaved with the same enzyme. Upon mixing the two linear plasmids, their complimentary single-stranded ends can pair with each other to form a single circle of DNA. The two plasmids can be joined covalently by use of a second enzyme known as polynucleotide ligase.

The above procedure can also be used to insert a fragment of DNA from an eukaryote into pUC3. For example, the DNA which codes for ribosomal RNA in the frog can be mixed with pUC3 DNA that has been cleaved. The resulting circular DNA molecules consist of plasmid pUC3 with an inserted length of frog rDNA.

The recombinant plasmids containing a desired genetic element, prepared by using pUC3, can be introduced into a host organism for expression. Examples of valuable genes which can be inserted into a host organism by the above described process are genes coding for somatostatin, rat proinsulin, and proteases.

The usefulness of plasmid pUC3 is that it represents a plasmid vector which functions in the industrially important microorganisms of the genus Streptomyces.

Hence, cloning of genetic information from Streptomyces onto pUC3 provides a means of increasing the production of commercially important products from these organisms, e.g. antibiotics.

This approach is compared to the concept of cloning genes for antibiotic production into the well characterized *Escherichia coli* K-12 host-vector system. The *E. coli* system has the disadvantage that it has been found that genes from some Gram-positive organisms, e.g. Bacillus, do not express well in the Gram-negative *E. coli* host. Likewise, plasmids from Gram-negative organisms are not maintained in Gram-positive hosts, and Gram-negative genetic information is either expressed poorly or not at all in Gram-positive hosts. This clearly argues for the advantage of a Gram-positive host-vector system and argues for the usefulness of plasmid pUC3 in such a system.

In general, the use of a host-vector system to produce a product foreign to that host requires the introduction of the genes for the entire biosynthetic pathway of the product to the new host. As discussed above, this may lead to problems of genetic expression, but may also generate new and/or increased problems in the fermentation of the microorganisms and in the extraction and purification of the product. A perhaps more useful approach is to introduce a plasmid vector, e.g. pUC3, into a host which normally produces the product and clone onto that plasmid the genes for biosynthesis of the product. At the very least, problems of fermentation and product extraction and purification should be minimized. Additionally, in this cloning system it may not be necessary to clone and amplify all the genes of the biosynthetic pathway, but rather it may be necessary only to clone regulatory genes or genes coding for the enzymes that are rate limiting in product biosynthesis. Since pUC3 is a streptomycete plasmid, it is ideally suited for these purposes in the genus Streptomyces. Furthermore, since pUC3 is also a plasmid from a Gram-positive organism, it may serve as a vector in a number of other microorganisms, e.g. Bacillus, Arthrobacter, etc.

The work described herein was all done in conformity with physical and biological containment requirements specified in the NIH Guidelines.

The restriction endonuclease map for pBR322 is published; Sutcliff, J. G. pBR322 restriction map derived from the DNA sequence: accurate DNA size markers up to 4361 nucleotide pairs long. Nucleic Acids Research 5, 2721–2728, 1978. This map is incorporated herein by reference to the above publication.

The novel hybrid plasmids of the subject invention are characterizable by reference to the maps for pUC3 and pBR322.

We claim:
1. *E. coli* HB101 (pUC1009) having the desposit accession number NRRL B-12005.
2. *E. coli* HB101 (pUC1010) having the deposit accession number NRRL B-12006.
3. *E. coli* HB101 (pUC1011) having the deposit accession number NRRL B-12007.
4. Hybrid plasmid pUC1009 characterized as follows:
    (a) it is a hybrid plasmid which has the entire nucleotide sequence of plasmid pBR322 and a foreign DNA insert at the BamH-1 site of pBR322;
    (b) said DNA insert being the 19 kb fragment of plasmid pUC3 shown in the drawing.
5. Hybrid plasmid pUC1010 characterized as follows:
    (a) it is a hybrid plasmid which has the entire nucleotide sequence of plasmid pBR322 and a foreign DNA insert at the BAMH-1 site of pBR322;
    (b) said DNA insert being the 5.7 kb fragment of plasmid pUC3 shown in the drawing.
6. Hybrid plasmid pUC1011 characterized as follows:
    (a) it is a hybrid plasmid which has the entire nucleotide sequence of plasmid pBR322 and a foreign DNA insert at the BamH-1 site of pBR322;
    (b) said DNA insert being the 5.7, 4.1 and 2.7 kb fragments of plasmid pUC3 shown in the drawing.

* * * * *